Nov. 17, 1942. N. S. RIVERS Plant Pat. 554
ORNAMENTAL PLANT VINE
Filed June 1, 1942
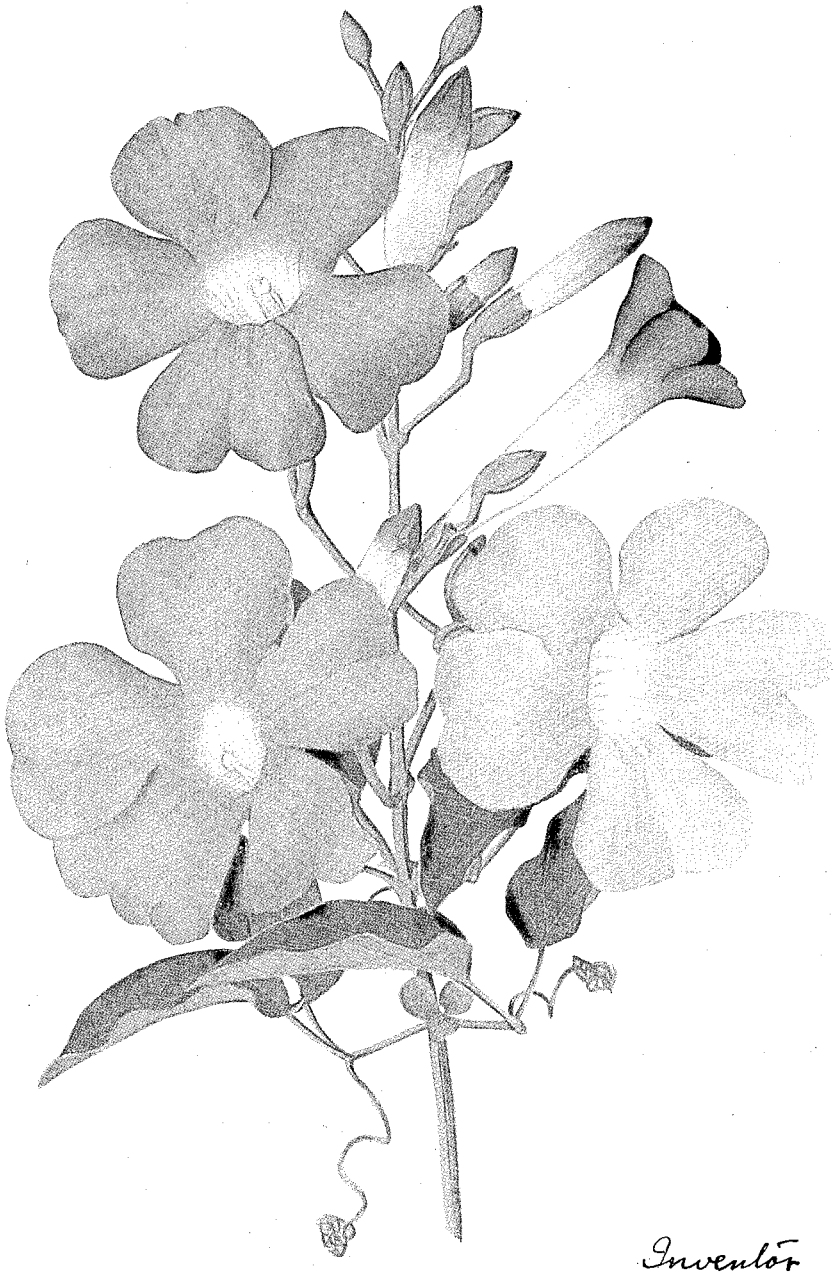
Inventor
N. S. Rivers
By Robert Robb
Attorneys Patented Nov. 17, 1942

Plant Pat. 554

UNITED STATES PATENT OFFICE

554

ORNAMENTAL PLANT VINE

Nairn Stowell Rivers, Santa Monica, Calif., assignor to Armstrong Nurseries, Inc., Ontario, Calif., a corporation of California Application June 1, 1942, Serial No. 445,363

1 Claim. (Cl. 47—60)

The present invention relates to a new and distinct variety of ornamental vine of the Bignoniaceae family, originated by crossing *Distictis laxiflora* and a similar vine identified as *Phaedranthus buccinatorius*.

Its particular claim to novelty resides in the entirely new shade of color for these flowers of the Bignoniaceae family, this color being according to Ridgway's color standards and nomenclature, near Purple (true), Plate XI, veined near Aster Purple, Plate XII, with the Purple changing abruptly but irregularly at the point where the base of the limb lobes joins inside of the corolla tube to near Lemon Chrome, Plate IV, on the inside surface of the limb lobe. It will be noted that in this respect this characteristic differs from *Phaedranthus buccinatorius* which is distinctly colored in the red tones on the inner surface of the limb lobe.

In addition to these color features illustrated in the accompanying drawing as nearly true as possible, the new variety is distinctive as to size and shape of the flower in comparison with other similar varieties grown under comparable conditions, resembling more nearly that of *Phaedranthus buccinatorius* than is common in the parent *Distictis laxiflora*. Sometimes it approaches nearly six inches in length, whereas in the parent *Dististis laxiflora*, the tubular flowers are seldom more than three and a half inches in length.

This new variety, likewise, compares in habit of growth and vigor more closely to that of *Phaedranthus buccinatorius* than to its other parent.

Also, more similar to *Phaedranthus buccinatorius* is the flowering habit which is intermittent throughout the year in mild climates, such as Southern California, in the vicinity of Santa Monica.

The foliage of this new variety is very glossy when mature, and, therefore, with these particular features in mind, it is claimed that this seedling of *Distictis laxiflora* is a distinctly new variety, not only because of its wide difference from its seed parent, but from other known members of the Bignoniaceae family as well.

The following is a detailed description of this new ornamental vine, the color terminology employed therein being in accord with Ridgway's Color Standard:

Type: Half-tender; tall; woody; vine; monoecious; gamopetalous; seedling; outdoor plant for garden decoration.

Class: Seedling.

*Seed parent.—Distictis laxiflora.*

*Pollen parent.—Phaedranthus buccinatorius.*

Propagation: The distinguishing characteristics have been found to come true to form by the following method of reproduction which is the only one tried up to this time: by cuttings.

*Flower*

Locality where grown: First grown at Santa Monica, California, and then moved to Mandeville Canyon, West Los Angeles, California.

Flowers borne: Two, four to several to stem; mostly terminal on lateral branches, mostly erect, panicles or racemes, with strong pedicels; with both short and long peduncles arranged in pairs of opposite flowers; each successive pair arranged in position on stem above at right angles to its predecessor (decussate); sometimes this arrangement is compound but always dichotomous.

Quantity of bloom: Free; outdoors.

Continuity: Intermittent to nearly continuous in mild climates, such as southern California.

Fragrance: None (seed parent vanilla scented).

Pedicel: Medium heavy; ¾'' to 2'' long, covered with pubescence and straight with distinct abscission layer soon formed between upper end and bending stalk of receptacle, allowing old flowers to drop off at end of usefulness.

*Color.*—Near Courge Green, Plate XVIII, on shaded side, near Olive Green, Plate IV, on sunny side.

Flower:

*Size.*—When fully open, large; 2½'' to 3½'' in diameter.

*Length of tube.*—2½'' to 4'', depending on mildness of weather condition at time of bloom, but never in any case as small as those of the seed parent.

*Petalage.*—Single.

*Form.—Bloom.*—five lobed, tubular-funnel form; symmetrical. Sympetalous and symsepalous; thick; leathery. Inside—velvety; smooth except for noticeable veining. Outside—satiny and covered with short pubescence.

*Shape of limb lobes.*—Emarginate—ovate sometimes emarginate-truncate with one notch; imbricate in bud. *Size*—1⅜'' to 1½'' broad and usually about 1¼'' long. *Color*—modified by being veined with more intense shadings of same colors.

This description of a newly opened flower was made from a plant grown outdoors in September, 1941, at Rivers Road, West Los Angeles, California:

*Color.*—Outside surface—near Bishop's Purple, Plate XXXVII, changing abruptly at point where base of limb lobe joins outside of corolla tube. Corolla tube vari-colored near Purplish Lilac, Plate XXXVII, on the upper side (side exposed to most sun), blending gradually toward under side to near Primrose Yellow, Plate XXX. Upper side of tube lightly penciled with also parallel lines running from base to tip with near Argyle Purple, Plate XXXVII. Upper side of corolla tube changes abruptly at extreme base to near Chalcedony Yellow, Plate XVII. Under side of corolla tube changes abruptly at extreme base to between Chalcedony Yellow, Plate XVII, and Chartreuse Yellow, Plate XXXI. Inside surface—limb lobes near Purple, (true), Plate XI, veined near Aster Purple, Plate XII. Purple changes abruptly but irregularly at point where base of limb lobes join inside of corolla tube, to near Lemon Chrome, Plate IV.

*Two-day flower.*—Inside surface—limb lobes near Pansy Violet, Plate XI, veined with Purple (true), Plate XI, irregularly, at point where base of limb lobe joins inside of corolla tube, to near Lemon Chrome, Plate IV. Outside surface—petals between Ageratum Violet, Plate XXXVII, and Argyle Purple, Plate XXXVII, blending gradually, at point where base of petal joins corolla tube, to near Purplish Lilac, Plate XXXVII, on upper side of corolla tube, and to between Pale Lobelia Violet, Plate XXXVII, and White on under side of corolla tube. Flower does not pull out of calyx tube second day.

This description was made from a plant that was open for three days outdoors in the month of September, 1941, at Rivers Road, West Los Angeles, California:

*Color.*—Outside petal, outside surface—petal between Chinese Violet, Plate XXV, and Lilac, Plate XXV, blending gradually at point where base of petal joints corolla tube, to near Purplish Lilac, Plate XXXVII, with some nearly parallel pencilings running from base to near the top of corolla tubes (more prominent near base) of near Argyle Purple, Plate XXXVII, on the upper side of corolla tube. Under side of corolla tube changes abruptly to between Pale Lilac, Plate XXXVII, and White. Point of attachment between Napthalene Yellow, Plate XVI, and Barium Yellow, Plate XVI, all around base of tube at point of attachment. (This color is not seen until corolla tube is slipped or pulled out of the monosepalous calyx tube, and the color dividing line is conspicuous by reason of the distinct break in color). Inside surface—near Argyle Purple, Plate XXXVII, blending toward the border of each petal to near Ageratum Violet, Plate XXXVII. Toward lower half of petal color changes abruptly to near Liseran Purple, Plate XXVI, and Rose Purple, Plate XXVI, at point where base of petal joins inside of corolla tube which in turn changes abruptly and irregularly at top end of corolla tube to between Ochraceous Buff, Plate XV, and Ochraceous Orange, Plate XV, with irregular but almost parallel pencilings, running from base to top of corolla tube, of near Lemon Chrome, Plate IV. Pencilings blend abruptly into the color adjacent to them which is usually between Ochraceous Buff, Plate XV, and Ochraceous Orange, Plate XV. The above colors all change abruptly to Citron Yellow, Plate XVI, at point of attachment.

*Reproductive organs*

Stamens: Five stamens; epigynous arranged regularly about pistil; usually included; four fertile, one sterile; polydelphous. Fertile stamens didynamous, longer pair almost as long as corolla, shorter pair approximately ⅔ as long as corolla, and sterile stamen usually less than ½ length of shorter pair of fertile stamens. Stamens attached to corolla at point where corolla emerges from tubular calyx.

Filaments: Unequal in length. *Color*—near Martius Yellow, Plate IV, except at extreme base where color changes abruptly to near Lemon Chrome, Plate IV.

Anthers: Large; all open at once; open by slits; attached versatile. *Color*—near Empire Yellow, Plate IV.

Pollen: Abundant. *Color*—near Empire Yellow, Plate IV.

Pistil: Simple. Densely pubescent at base becoming smooth toward stigma.

Stigma: Two, parted. *Color*—near Deep Sea Foam Green, Plate XXXI; each part spatulate in shape.

Style: Long; hairy. Usually equal in length, or nearly so, to the longer pair of stamens (usually in excess of 2″). *Color*—between Pale Glass Green, Plate XXXI, and White.

Ovary: Number of ovules not known; arrangement on placenta parietal, axillary.

Calyx: Persistent; campanulate; 5 denticulate. *Color*—between Biscay Green, Plate XVII, and Courge Green, Plate XXXI, overlaid with markings of near Dark Vinaceous Brown, Plate XXXIX. Fine woolly tomentum may be seen on close observation.

Form: Symsepalous—length of calyx tube $\frac{7}{16}$″ to ¾″. Tomentulose outside, short pubescence inside.

Seeds: No seeds set.

Fruits: None yet set.

*Plant*

Foliage: Leaves and leaflets: Evergeen; petiole—medium. Length—2¾″ to 3¼″ average. Width—1½″ to 1⅝″ average. Arranged opposite, normal—average size 1″ wide and 2⅛″ long, glabrous above, tomentose beneath particularly on mid-rib and veins; medium thick, semi-glossy above; leathery; compound of two leaflets, a middle third differentiated into a twining tendil which is three-parted, each part ending in a vacuum cup attaching to any available support. Petioles hairy beneath, somewhat more densely hairy and grooved above.

*Shape.*—Lanceolate, ovate.

*Apex.*—Acuminate.

*Base.*—Cordate, sometimes.

*Margins.*—Entire, usually somewhat wavy or undulating.

*Immature leaf.*—*Color*—upper surface near Light Cress Green, Plate XXXI. *Midrib*—near Chrysolite Green, Plate XXXI, changing toward point of attachment to between Rainette Green and Light Cress Green, both Plate XXXI. *Veins*—near Chrysolite Green, Plate XXXI. Under surface near Light Elm Green, Plate XVII. *Midrib*—near Rainette Green, Plate XXXI, at point of attachment, changing gradually toward apex to near Citron Green, Plate XXXI. *Veins*—near Kildare Green, Plate XXXI. *Net veins*—numerous but same as under surface color, near Light Elm Green, Plate XVII.

*Mature leaves.*—Upper surface—*color*—upper surface near Cress Green, Plate XXXI, some between Cress Green and Dark Cress Green, Plate XXXI. *Midrib*—near Chrysolite Green, Plate XXXI, changing to near Rainette Green, Plate XXXI, with an overlay of near Light Seal Brown, Plate XXXIX, at point of attachment. *Net veins*—between Chrysolite Green, and Kildare Green, plate XXXI. Under surface—*color*—under surface near Light Cress Green, Plate XXXI. *Midrib*—near Deep Chrysolite Green, Plate XXXI, at point of attachment, blending gradually to near Deep Sea Foam Green, Plate XXXI, changing gradually toward tip to near Pale Glass Green, Plate XXI. Veins between Deep Sea Foam Green and Pale Glass Green, Plate XXI. *Net veins*—much net veined with between Chrysolite Green, and Light Cress Green, Plate XXXI.

*Petiole.*—Medium, the two opposite cooperating to encircle stem. Upper side—grooved; hairy. Under side—sparsely hairy.

*Stipules.*—None.

*Diseases.*—Resistant, insofar as this is evidenced by absence of any disease throughout development and establishment of this variety.

Growth:

*Habit.*—Climbing; much branched. Climbing by tendrils terminated by vacuum cups which create suction.

*Growth.*—Very vigorous, to fifty feet or more.

*Main stems.*—Much branched, medium, slender.

*Branches.*—*Color*—under side—near Courge Green, Plate XVII. Upper side—(side exposed to most sun) near Rainette Green with overlay of near Light Seal Brown, Plate XXXIX; pubescent.

*Bark.*—Somewhat shredding with age.

I claim:

A new and distinct variety of ornamental vine of the Bignoniaceae family, characterized as to novelty by its vigorous growth to great height, its glossy foliage, and the color combination, size and shape of its flowers, substantially as shown and described.

NAIRN S. RIVERS.